United States Patent [19]

Kaplan

[11] Patent Number: 4,485,268
[45] Date of Patent: Nov. 27, 1984

[54] SEALING DEVICE FOR AN ELECTRICAL CONNECTOR AND METHOD THEREFOR

[75] Inventor: Morton R. Kaplan, Santa Barbara, Calif.

[73] Assignee: Minnesota Mining and Manufacturing, St. Paul, Minn.

[21] Appl. No.: 503,855

[22] Filed: Jun. 13, 1983

[51] Int. Cl.³ .................. H02G 15/08; A61N 1/04
[52] U.S. Cl. ..................... 174/84 C; 29/862; 72/410; 128/784; 128/785; 174/71 R; 174/76; 174/138 F
[58] Field of Search ............ 174/71 R, 76, 84 C, 174/138 F; 29/862, 863; 128/419 P, 642, 784, 785, 786

[56] References Cited

U.S. PATENT DOCUMENTS

| | | |
|---|---|---|
| 2,785,319 | 3/1957 | Simpson et al. ............ 174/71 R |
| 3,340,493 | 9/1967 | Fisher et al. . |
| 3,659,615 | 5/1972 | Enger ..................... 128/419 PS X |
| 3,783,177 | 1/1974 | Kelso . |
| 4,012,103 | 3/1977 | Lunquist ................. 128/419 P X |
| 4,025,717 | 5/1977 | Whittingham . |
| 4,061,872 | 12/1977 | DeMonsy et al. . |
| 4,176,245 | 11/1979 | Merlack et al. ............ 174/76 X |
| 4,196,308 | 4/1980 | Siden .................... 174/84 C |
| 4,214,594 | 7/1980 | Little . |
| 4,226,651 | 10/1980 | Gold . |
| 4,236,525 | 12/1980 | Sluetz et al. . |
| 4,314,095 | 2/1982 | Moore et al. . |
| 4,316,471 | 2/1982 | Shipko et al. . |
| 4,319,578 | 3/1982 | Enger ..................... 128/635 |
| 4,325,389 | 4/1982 | Gold . |
| 4,387,727 | 6/1983 | Sandstrom ............... 128/419 P |
| 4,403,110 | 9/1983 | Morrisette .............. 174/76 X |
| 4,411,277 | 10/1983 | Dickhudt ................. 128/784 |

OTHER PUBLICATIONS

Glenn, *Annals of the New York Academy of Sciences*, vol. III, Article III, Jun. 11, 1964, p. 1114.
Pialous, Chouard and MacLeod, *First International Course on Multichannel Cochlear Implant*, Paris, Sep. 21-24, 1978, Section IV, Material Preparation.

*Primary Examiner*—John F. Gonzales
*Assistant Examiner*—Morris H. Nimmo
*Attorney, Agent, or Firm*—Donald M. Sell; James A. Smith; William D. Bauer

[57] ABSTRACT

A sealing device for a wire splice. An insulative tube with a reservoir positioned transverse to and communicating with the insulative tube is adapted to receive a wire splice. A septum within the reservoir at least partially divides the reservoir substantially transverse to the insulative tube. An insulative fluid may then be forced through the reservoir into the insulative tube surrounding the wire splice. A connector for electrical wires is formed from a conductive tube adapted to receive the ends of the electrical wires to be connected and capable of being crimped onto the electrical wires. A sealing device may then be positioned over the conductive tube and an insulative viscous fluid may be forced through the reservoir into the insulative tube surrounding the conductive tube in order that the electrical wires may be electrically connected and insulated.

16 Claims, 7 Drawing Figures

SEALING DEVICE FOR AN ELECTRICAL CONNECTOR AND METHOD THEREFOR

BACKGROUND OF THE INVENTION

The present invention relates generally to sealing devices for electrical connectors and more particularly to sealing devices for electrical connectors where the electrical connector is implanted within the body.

With the increasing use of implantable electronics, there is an increasing need for a device for and method of securely connecting the ends of two or more electrical wires and sealing the connector from the corrosive effects of the body, especially the human body.

Cochlear implants frequently involve inserting an electrode into the cochlea. When connected to suitable electronics this electrode produces the electrical stimulation of the auditory nerve which may represent a sensation of hearing in some persons. Often the electrode positioned in the cochlea is coupled directly to associated electronics with a continuous wire. Sometimes it is necessary or desired to change the associated electronics. Typically this is due either to a failure in the electronics or the desire to update the electronics to a more advanced version. Usually it is undesireable to replace the electrode at the same time. After the electrode is inserted into the cochlea, tissue grows around the electrode, making the removal and successful reinsertion of another electrode very difficult. Therefore, it is preferable to be able to cut the wire to the present electrode and to be able to connect a new wire and new associated electronics to that wire.

An electrical connector implanted in the body must be very reliable since surgery would be required to repair the connection. Even though the loss of hearing is not in itself life threatening, unnecessary surgery should be avoided. The electrical connector itself should be solid and secure. The connector should be protected from the severe corrosive environment of the body and the electrical connection should be electrically insulated from the body. The connector and its sealing mechanism should not be toxic to its host.

In order to seal an implanted electrical connection, it is known to slip an insulative tube over the connection and to fill the internal space around the connection within the insulated tube with a suitable sealing material, such as silicone rubber. Reference is made to a first international course on multi-channel cochlear implant presented in Paris on September 1-24, 1978, in an article by Chouard, Pialoux and MacLeod.

A major problem, however, is to provide a mechanism to enable the sealing material, e.g. silicone rubber, to be forced into the insulative tube easily and reliably so that the surgeon can accomplish the connection and sealing quickly and with confidence. The sealing material must completely surround the connection, preferably filling all voids between the insulative tube and the connection.

If sealing material is forced into one end of the tube, there is no guarantee that the sealing material will reliably fill all air spaces before being forced out the opposite end of the tube. If air spaces remain, the "voids" could effect the reliability of the seal and the resultant reliability of the electrical connection.

SUMMARY OF THE INVENTION

A sealing device for a wire splice is provided including an insulative tube adapted to receive the wire splice, a reservoir positioned transverse to and communicating with the insulative tube and a septum within said reservoir at least partially dividing the reservoir substantially transverse to the insulative tube. With this sealing device an insulative viscous fluid may be placed within the reservoir and may be forced from the reservoir into the insulative tube surrounding the wire splice.

In a preferred embodiment, the septum divides the reservoir at the point where the reservoir communicates with the insulative tube. In a preferred embodiment, the reservoir is shaped to be elongate along the axis of the insulative tube. In a preferred embodiment, the insulative tube and the reservoir are constructed from a silicone polymer and in a preferred embodiment the insulative tube and the reservoir are biocompatible.

The invention also consists of a connector for electrical wires which includes a conductive tube adapted to receive the ends of the electrical wires to be connected and capable of being crimped onto the electrical wires, an insulative tube adapted to be positioned over the conductive tube, a reservoir positioned transverse to and communicating with the insulative tube and positioned near the conductive tube, and a septum located within the reservoir at least partially dividing the reservoir substantially transverse to the insulative tube. With this connector an insulative viscous fluid may be forced from the reservoir into the insulative tube surrounding the conductive tube in order that the electrical wires may be electrically connected and insulated.

The present invention also consists of a method of making an insulated, implantable, electrical connection which includes the steps of slipping an insulator, the insulator consisting of an insulative tube with a reservoir positioned transverse to and communicating with the insulative tube with an internal septum located within the reservoir at least partially dividing the reservoir transverse to the insulative tube, over a first wire to be connected, inserting the first wire to be connected and the second wire to be connected into a crimpable conductive tube, crimping the conductive tube to both the first and second wires, repositioning the insulative tube over the conductive tube and forcing an insulative viscous fluid from the reservoir into the insulative tube to surround the conductive tube.

The laterally positioned reservoir containing the septum is the feature that faciliates the easy and reliable sealing of an implanted electrical connection. The lateral reservoir helps ensure that air spaces in the central interior area of the tube are filled with sealing material. The sealing material, being introduced here, must fill the central area before being forced out the ends of the tube. If no septum is present in the reservoir, the sealing material often goes toward one end of the tube without adequately filling the tube toward the opposite end. With a septum present in the reservoir, the sealing material is forced from the reservoir on one side of the septum into the tube, the sealing material will flow toward the near end of the tube filling it with such sealing material. Sealing material is then (or simultaneously) forced into the tube from the other side of the septum, and will flow toward the remaining tube end filling it with such sealing material. Thus, it is ensured that the sealing material will fill air spaces in both ends and the central area of the insulative tube.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
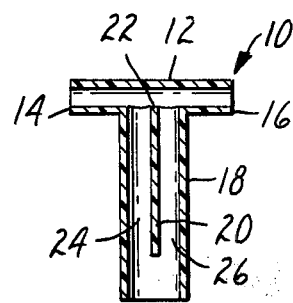
FIG. 1 is a side view of the sealing device of the present invention.

The sealing device illustrated in FIG. 1 is intended to be placed over a completed electrical connection of two wires which have been implanted in the body in order to seal the connected wires against the body's environment. The sealing device 10, commonly known as a T-tube, has an elongated insulative tube 12 which is designed to be positioned over the completed electrical connection. The insulative tube has open ends 14 and 16 facilitating the entry of the two wires to be connected. A lateral reservoir 18 is positioned laterally transverse to the insulative tube 12 and communicating with it. A septum 20 partially divides reservoir 18 into two portions. In a preferred embodiment the septum 20 divides the reservoir 18 at or near the point 22 at the juncture of the reservoir 20 and the interior of the insulative tube 12. Although no specific shape for the reservoir 18 is required, it is preferred, and is illustrated in FIG. 1, that the reservoir 18 be elongate along the axis of the insulative tube 12. Also preferred, although not required, the septum 20 divides the reservoir into two equal portions laterally with respect to the insulative tube 12.

The septum 20 is required to divide the reservoir 18 into two portions with respect to the lateral dimension of the insulative tube 12 with respect to open ends 14 and 16. As previously mentioned the septum is not required to extend the entire lateral distance along reservoir 18 although it is preferred that the septum 20 divide the reservoir 18 at point 22 where it junctures with the inside diameter of insulative tube 12.

The insulative tube 12 and the material forming reservoir 18 should be formed of a biocompatible material so as to not be of harm to its host. The insulative tube 12 should be insulative. Generally in the biomedical field, insulative means a minimum of resistance of 2 kilohms and a resistance of at least 10 megohms is preferred. It is also preferred, although not required, that the insulative tube be somewhat flexible. The preferred material for the insulative tube 12 is a silicone polymer. It is preferable that the durometer of the silicone polymer be between 25 and 55 points, Shore A.

It is preferred, although not required, that the material forming the reservoir 18 also be flexible. The preferred material for the reservoir 18 is a silicone polymer and it is still preferred that the silicone polymer be the same as or similar to the silicone polymer used for the insulative tube 12.

The reservoir 18 can be constructed of a flexible material. In one embodiment chambers 24 and 26 of reservoir 18 can be prefilled with a suitable sealing material. That is, prior to delivery to the surgeon, chambers 24 and 26 of reservoir 18 can be filled with a suitable sealing material. The reservoir 18 may then be compressed by the surgeon at the time the sealing of the electrical connection is done to force the sealing material from chambers 24 and 26 of the reservoir 18 into the interior of the insulative tube 12.

However, it is preferred that chambers 24 and 26 of reservoir 18 not be prefilled with a sealing material. Chambers 24 and 26 then become a conduit to allow for passage of externally supplied sealing material at the time of installation and sealing of the electrical connection. A suitable supply mechanism is a syringe with an 18 gauge blunt needle.

The sealing material can be bone wax but it is preferred that a silicone polymer be utilized. An example of a suitable silicone polymer is a silicone medical grade adhesive. Specifically it is preferred that a Dow Corning Silastic Medical Grade Adhesive with a viscosity of approximately 800 poise be utilized. Dow Corning and Silastic are trademarks of the Dow Corning Corporation.

Figure 2:
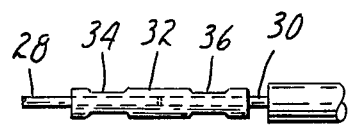
FIG. 2 illustrates a wire connection before sealing.

FIG. 2 illustrates a completed electrical connection, but not a completely sealed electrical connection, between wires 28 and 30. Wires 28 and 30 are inserted in opposite ends of a conductive tube 32. The conductive tube is then crimped at locations 34 and 36 onto wires 28 and 30, respectively, making a physical and electrical connection. In a preferred embodiment the conductive tube is constructed of platinum and the wires 28 and 30 are also preferred to be platinum. The crimping of the conductive tube 32 to wires 28 and 30 is a standard, well known medical technique.

Figure 3:
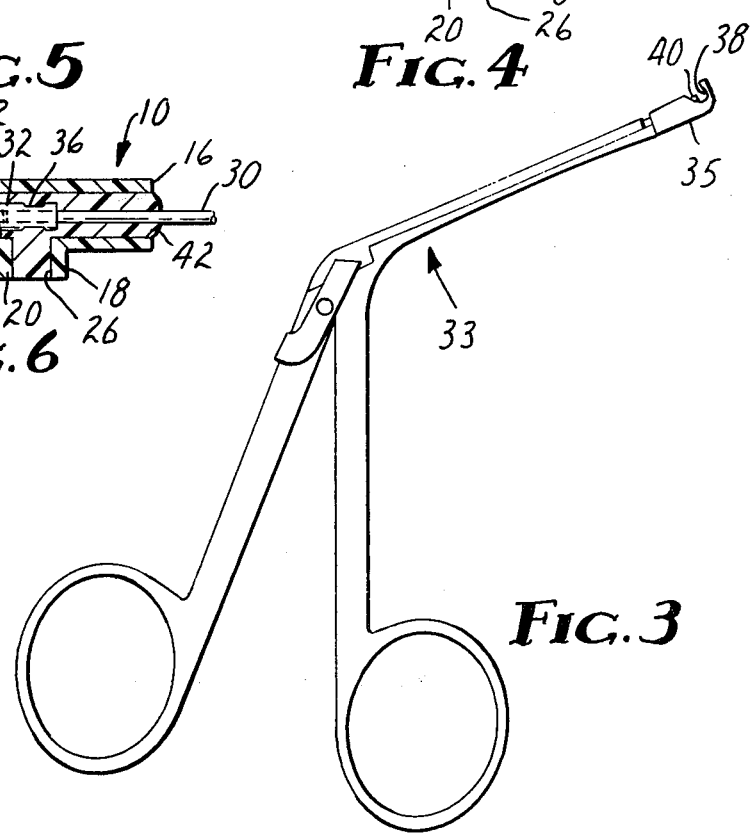
FIG. 3 illustrates a crimping tool used to make the connection of FIG. 2.

Many tools can be used to perform the crimping operation illustrated in FIG. 2. A preferred tool 33 is illustrated in FIG. 3. The tool 33 may be constructed from a pair of Belucci pliers modified to provide the crimping end 35. To utilize the tool 33, the tool 33 is positioned around the conductive tube 32 at location 34 or 36 so that the conductive tube 32 is positioned in the rounded portion 38 in the crimping end 35 of the tool 33. The rounded portion 38 serves to easily hold the conductive tube 32 in place. A rod 40 operated from the handles of the tool 33 then crimps the conductive tube 32 as the handles are squeezed. The use of the tool 33 makes it easy for the surgeon to get and crimp the conductive tube 32 in hard to reach areas of the body during surgery.

Figure 5:
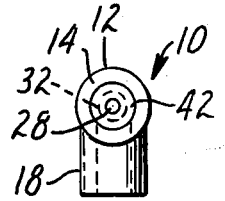
FIG. 5 is an end view of FIG. 4.
Figure 4:
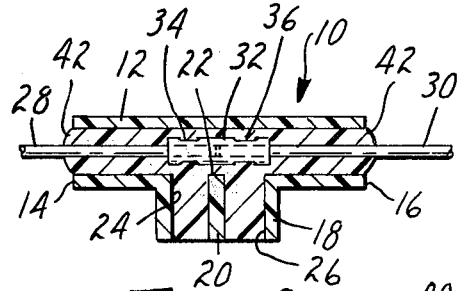
FIG. 4 is am embodiment of the sealing device of the present invention in place over a wire connection forming a complete electrical connection.

FIGS. 4 and 5 show the sealing device of the present invention in place forming the completed connector for electrical wires 28 and 30. As illustrated in FIG. 2, wires 28 and 30 have been crimped together over a conductive tube 32. The sealing device is repositioned with the insulative tube 12 positioned directly over the crimped conductive tube 32. Reservoir 18 is shown forming chambers 24 and 26 which are divided by septum 20. Once the sealing device 10 is in place a sealing material 42 may be forced through chamber 24 into the interior of insulative tube 12 and either subsequently or simultaneously forced through chamber 26 into insulative tube 12. Having septum 20 form chambers 24 and 26 through which the sealing material may be forced ensures that the sealing material 42 may fill all voids within the central portion of the insulative tube 12 and flow toward end 14 and end 16 completely filling the interior of insulative tube 12 and ensuring the complete sealing of the electrical connection formed by conductive tube 32. As illustrated in FIG. 4 sealing material 42 has been forced through chambers 24 and 26 of the reservoir 18 into the interior of insulative tube 12 so that it protrudes slightly from ends 14 and 16 of the insulative tube 12. Also as illustrated in FIG. 4 it is preferred that the sealing device 10 be positioned approximately over the center of the crimped conductive tube 32.

Figure 6:
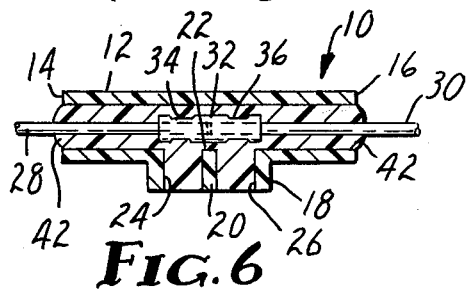
FIG. 6 is an illustration of the completed connection with optional trimming of the reservoir having been completed.

The completed electrical connection illustrated in FIG. 6 illustrates that, as an optional step, the reservoir 18 may be trimmed to near or at the outside dimension of the insulative tube 12 following the forcing of the sealing material from the reservoir 18 into the interior of insulative tube 12. The resulting trimming of the reservoir 18 results in a neater and smaller completed electrical connection.

Figure 7:
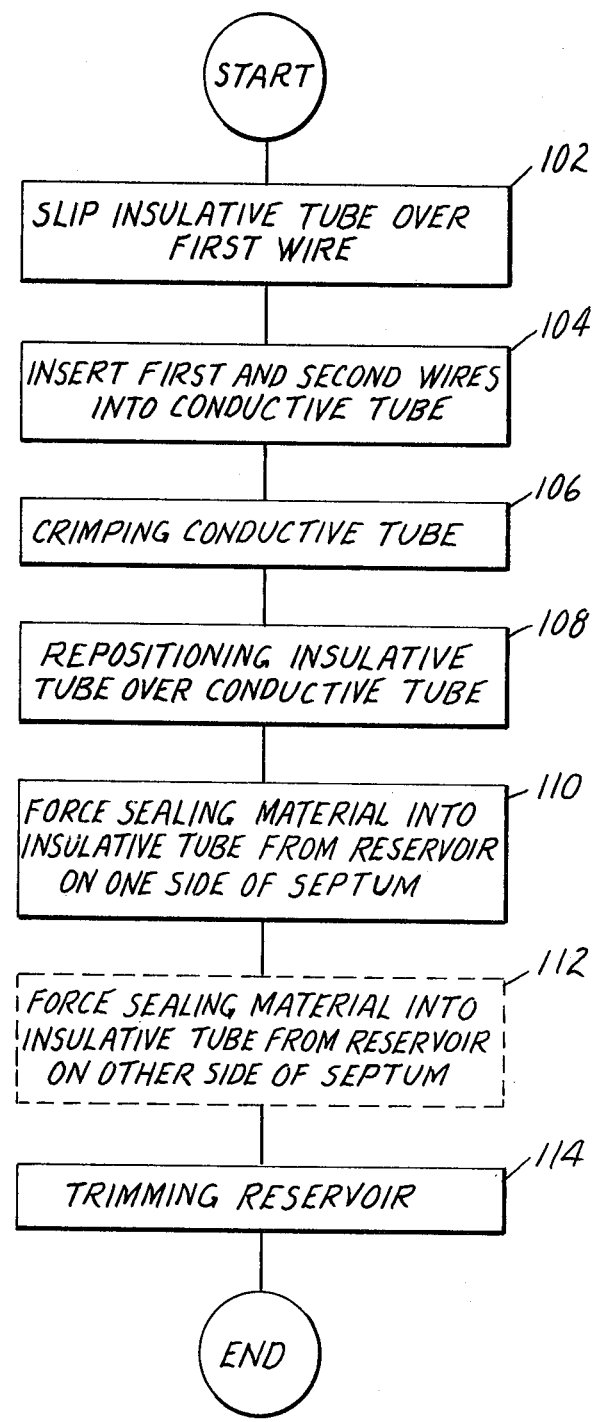
FIG. 7 is a flow diagram of the method of the present invention.

FIG. 7 illustrates a flow chart of the method of the present invention. The method is started by first slipping 102 the insulative tube 12 over a first wire 28 which is to be connected. The first and second wires 28 and 30 to be connected are inserted 104 into the conductive tube 32. The crimping 106 of the conductive tube 32 is then accomplished making a mechanical and electrical connection between wires 28 and 30. The insulative tube is then repositioned 108 over the conductive tube to facilitate the subsequent sealing of the electrical connection. The next step is to force 110 sealing material 42 into the insulative tube 12 from the reservoir 18 on one side of the septum 20 (e.g. chamber 24). The next step is to force 112 sealing material 42 into insulative tube 12 from the reservoir 18 on the other side of the septum 20 (e.g. chamber 26). Step 112 can be accomplished subsequent to step 110 or simultaneously with step 110. That is, the sealing material 42 may be forced through chambers 24 and 26 of reservoir 18 simultaneously into insulative tube 12 which will then force the sealing material 42 in opposite directions of the ends 14 and 16 of insulative tube 12 or the sealing material 42 may be forced first through chamber 24 (or chamber 26) into insulative tube 12 and out end 14 of the insulative tube. Subsequently sealing material 42 may be forced through chamber 24 (chamber 26) of reservoir 18 into the interior of insulative tube 12 and out end 16 of insulative tube 12. The reservoir 18 may then be trimmed 114 close to the outside diameter of insulative tube 12. Step 114, trimming, is an optional step.

Thus, it can be seen that there has been shown and described a novel sealing device for an electrical connector and method therefor. It is to be understood, however, that various changes, modifications and substitutions in the form of the details of the described invention can be made by those skilled in the art without departing from the scope of the invention as defined by the following claims.

What is claimed is:
1. A sealing device for a wire splice, comprising:
an insulative tube adapted to receive said wire splice;
a reservoir positioned transverse to and communicating with said insulative tube; and
a septum within said reservoir at least partially dividing said reservoir substantially transverse to said insulative tube;
whereby an insulative viscous fluid may be placed within said reservoir and may be forced from said reservoir into said insulative tube for surrounding said wire splice.

2. A sealing device as in claim 1 wherein said septum divides said reservoir at the point where said reservoir communicates with said insulative tube.

3. A sealing device as in claim 2 wherein said reservoir is shaped to be elongate along the axis of said insulative tube.

4. A sealing device as in claim 3 wherein said insulative tube and said reservoir are constructed from a silicone polymer.

5. A sealing device as in claim 4 wherein said insulative tube and said reservoir are biocompatible.

6. A sealing device for a wire splice, comprising:
an insulative tube adapted to receive said wire splice;
a reservoir positioned transverse to and communicating with said insulative tube;
a septum within said reservoir at least partially dividing said reservoir substantially transverse to said insulative tube; and
an insulative viscous fluid located within said reservoir on both sides of said septum;
whereby said insulative viscous fluid may be forced from said reservoir into said insulative tube for surrounding said wire splice.

7. A sealing device as in claim 6 wherein said septum divides said reservoir at the point where said reservoir communicates with said insulative tube.

8. A sealing device as in claim 7 wherein said reservoir is shaped to be elongate along the axis of said insulative tube.

9. A sealing device as in claim 7 wherein said insulative tube and said reservoir are constructed from a silicone polymer.

10. A sealing device as in claim 7 wherein said insulative viscous fluid is bone wax.

11. A sealing device as in claim 7 wherein said viscous fluid is a medical grade silicone elastomeric polymer.

12. A connector for electrical wires, comprising:
a conductive tube adapted to receive the ends of said electrical wires to be connected and capable of being crimped onto said electrical wires;
an insulative tube adapted to be positioned over said conductive tube;
a reservoir positioned transverse to and communicating with said insulative tube and positioned near said conductive tube;
a septum located within said reservoir at least partially dividing said reservoir substantially transverse to said insulative tube; and
whereby an insulative viscous fluid may be forced from said reservoir into said insulative tube surrounding said conductive tube in order that said electrical wires may be electrically connected and insulated.

13. A connector as in claim 12 wherein said septum is positioned over said conductive tube.

14. A connector as in claim 13 wherein said reservoir is shaped to be elongate along the axis of said insulative tube.

15. A connector as in claim 14 wherein said insulative tube and said reservoir are constructed from a silicone polymer.

16. A method of making an insulated implantable electrical connection, comprising the steps of:
slipping an insulator, said insulator consisting of insulative tube with a reservoir positioned transverse to and communicating with said insulative tube with an internal septum located within said reservoir at least partially dividing said reservoir transverse to said insulative tube, over a first wire to be connected;

inserting said first wire to be connected and a second wire to be connected into a crimpable, conductive tube;

crimping said conductive tube to both said first and second wires;

repositioning said insulative tube over said conductive tube; and forcing an insulative viscous fluid from said reservoir into said insulative tube to surround said conductive tube.

* * * * *